United States Patent [19]

Bird et al.

[11] Patent Number: 4,664,693
[45] Date of Patent: * May 12, 1987

[54] 5-[SUBSTITUTED BICYCLIC ARYL OR HETEROARYL]CYCLOHEXANE-1,3-DIONE HERBICIDES

[75] Inventors: Graham J. Bird, North Melbourne; Graeme J. Farquharson, Reservoir; Keith G. Watson, Box Hill North; Murray L. Whitelaw, Carlton, all of Australia

[73] Assignee: ICI Australia Limited, Melbourne, Australia

[*] Notice: The portion of the term of this patent subsequent to Apr. 16, 2002 has been disclaimed.

[21] Appl. No.: 600,072

[22] Filed: Apr. 13, 1984

[30] Foreign Application Priority Data

May 6, 1983 [AU] Australia ............................... PF9197

[51] Int. Cl.⁴ ................. C07D 333/54; C07D 307/79; A01N 43/02; A01N 43/00
[52] U.S. Cl. ........................................ 71/88; 549/51; 549/54; 549/55; 549/56; 549/57; 549/58; 549/466; 549/467; 549/468; 549/469; 549/470; 549/471; 71/90
[58] Field of Search ............... 549/466, 467, 468, 469, 549/470, 471, 51, 54, 55, 56–58; 71/88, 90

[56] References Cited

U.S. PATENT DOCUMENTS 3,950,420 4/1976 Sawaki et al. ........................... 71/88
4,033,754 7/1977 Sawaki et al. ......................... 71/106
4,511,391 4/1985 Serban et al. ............................ 71/88

FOREIGN PATENT DOCUMENTS 3230087 2/1984 Fed. Rep. of Germany .......... 71/90

Primary Examiner—George F. Lesmes
Assistant Examiner—S. A. Gibson
Attorney, Agent, or Firm—Cushman, Darby & Cushman

[57] ABSTRACT

The invention concerns novel compounds of the formula I

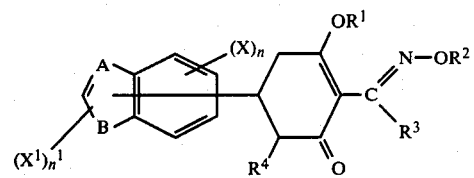

wherein:
A is selected from CH and N;
B is selected from oxygen, sulfur, $CH_2$ and the group N-Z wherein Z is selected from the group consisting of hydrogen, alkyl, alkenyl, alkynyl, cycloalkyl, benzyl and substituted benzyl;
X, which may be the same or different, and $X^1$, which be the same or different, are selected from halogen, nitro, cyano, alkyl, substituted alkyl, hydroxy, alkoxy, substituted alkoxy, alkenyl, alkenyloxy, alkynyl, alkynyloxy, acyloxy, alkoxycarbonyl, alkylthio, alkylsulfinyl, alkylsulfonyl, sulfamoyl, substituted sulfamoyl, alkanoyloxy, benzyloxy, substituted benzyloxy, amino, substituted amino, and the groups formyl and alkanoyl and the oxime, imine and Schiff base derivatives thereof;
$R^1$ is selected from hydrogen, alkyl, alkenyl, alkynyl, substituted alkyl, alkylsulfonyl, arylsulfonyl, acyl and an inorganic or organic cation;
$R^2$ is selected from alkyl, substituted alkyl, alkenyl, haloalkenyl, alkynyl and haloalkynyl;
$R^3$ is selected from alkyl, fluoroalkyl, alkenyl, alkynyl, and phenyl;
$R^4$ is selected from hydrogen, halogen, alkyl, cyano and alkoxycarbonyl;
n is 0 or an integer chosen from 1 to 4; and
$n^1$ is 0 or an integer chosen from 1 to 4.

The compounds of the invention show herbicidal properties and plant growth regulating properties and in further embodiments the invention provides processes for the preparation of compounds of formula I, intermediates useful in the preparation of the compounds of formula I, compositions containing as active ingredient a compound of formula I, and herbicidal and plant growth regulating processes utilizing compounds of formula I.

10 Claims, No Drawings

5-[SUBSTITUTED BICYCLIC ARYL OR HETEROARYL]CYCLOHEXANE-1,3-DIONE HERBICIDES

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes utilizing such compounds.

The use of certain cyclohexane-1,3-dione derivatives as grass herbicides is known in the art. For example, the "Pesticide Manual" (C R Worthing Editor, The British Crop Protection Council, 6th Edition 1979) describes the cyclohexane-1,3-dione derivative known commercially known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Australian Pat. No. 464 655 and its equivalents such as UK Pat. No. 1 461 170 and U.S. Pat. No. 3,950,420.

More recently, at the 1980 British Crop Protection Conference ("1980 British Crop Protection Conference—Weeds, Proceedings Vol 1, Research Reports", pp 39 to 46, British Crop Protection Council, 1980), a new cyclohexane-1,3-dione grass herbicide code named NP 55 (2-N-ethoxybutrimidoyl)-5-(2-ethylthiopropyl)-3-hydroxy-2-cyclohexen-1-one) was announced. This compound is disclosed in Australian Pat. No. 503 917 and its equivalents.

It has now been found that a new group of cyclohexane-1,3-dione derivatives which have a 5-indenyl or 5-(fused benzo-heterocyclopentenyl) substituent exhibit particularly useful herbicidal activity.

Accordingly the invention provides a compound of formula

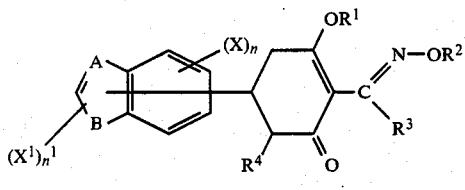

wherein:
A is selected from CH and N;
B is selected from oxygen, sulfur, $CH_2$ and the group N—Z wherein Z is selected from the group consisting of hydrogen, $C_1$ to $C_6$ alkyl, $C_2$ to $C_6$ alkenyl, $C_2$ to $C_6$ alkynyl, $C_3$ to $C_7$ cycloalkyl, benzyl and substituted benzyl wherein the benzene ring is substituted with from one to three substituents selected from the group consisting of halogen, nitro, $C_1$ to $C_6$ alkyl, $C_1$ to $C_6$ alkoxy, and $C_1$ to $C_6$ haloalkyl;
X, which may be the same or different, and $X^1$, which may be the same or different, are independently selected from the group consisting of: halogen; nitro; cyano; $C_1$ to $C_6$ alkyl; $C_1$ to $C_6$ alkyl substituted with a substituent selected from the group consisting of halogen, nitro, hydroxy, $C_1$ to $C_6$ alkoxy and $C_1$ to $C_6$ alkyllthio; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkenyloxy; $C_2$ to $C_6$ alkynyloxy; $C_2$ to $C_6$ alkanoyloxy; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, benzoyl and benzyl; the groups formyl and $C_2$ to $C_6$ alkanoyl and the oxime, imine and Schiff base derivatives thereof;
$R^1$ is selected from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ alkyl sulfonyl; benzenesulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation;
$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;
$R_3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl;
$R_4$ is selected from the group consisting of: hydrogen; halogen; cyano; $C_1$ to $C_6$ alkyl; and ($C_1$ to $C_6$ alkoxy)carbonyl;
n is 0 or an integer chosen from 1 to 4; and
$n^1$ is 0 or an integer chosen from 1 to 4.

When in the compound of formula I X is chosen from the groups formyl and $C_2$ to $C_6$ alkanoyl and the oxime, imine and Schiff base derivatives thereof, the nature of the oxime, imine and Schiff base derivatives is not narrowly critical. Although not intending to be bound by theory, it is believed that in the plant the (substituted) imine group may be removed to give the corresponding compound of formula I in which X is formyl of $C_2$ to $C_6$ alkanoyl. Suitable values for the groups formyl and $C_2$ to $C_6$ alkanoyl and the oxime, imine and Schiff base derivatives thereof include groups of the formula $-C(R^7)=NR^8$ wherein $R^7$ is chosen from hydrogen and $C_1$ to $C_5$ alkyl, and $R^8$ is chosen from hydrogen, $C_1$ to $C_6$ alkyl, phenyl, benzyl, hydroxy, $C_1$ to $C_6$ alkoxy, phenoxy and benzyloxy.

When in the compound of formula I $R^1$ is chosen from acyl the nature of the acyl group is not narrowly critical. Although not intending to be bound by theory, it is believed that when $R^1$ is acyl the acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and heteroaroyl, for example 2-furoyl, 3-furoyl, 2-thenoyl and 3-thenoyl.

When in the compound of formula I $R^1$ is chosen from an inorganic or organic cation the nature of the cation is not narrowly critical. Although not intending to be bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^9R^{10}R^{11}R^{12}N^+$ wherein $R^9$, $R^{10}$, $R^{11}$ and $R^{12}$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R_1$ is hydrogen the compounds of the invention may exist in any one of four tautomeric forms as shown below wherein $\phi$ represents the group

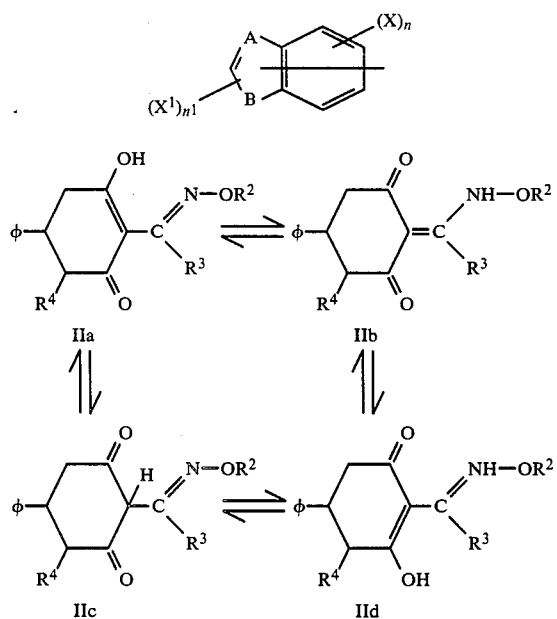

The compounds of the invention include:
indene derivatives of formula Ia

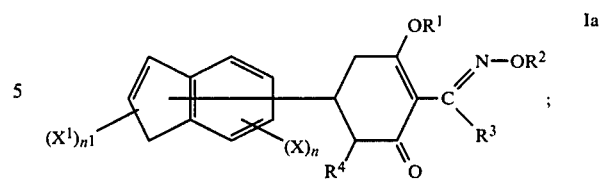

benzofuran derivatives of formula Ib

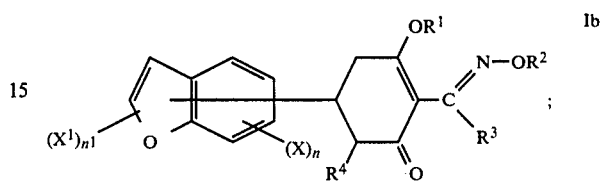

benzothiophene derivatives of formula Ic

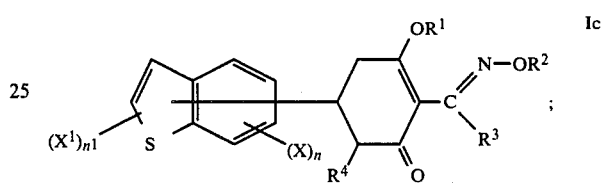

indole derivatives of formula Id and Ie

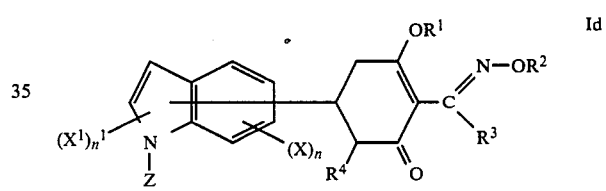

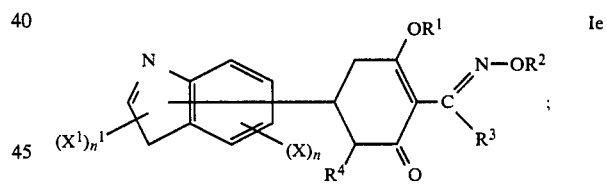

benzoxazole derivatives of formula If

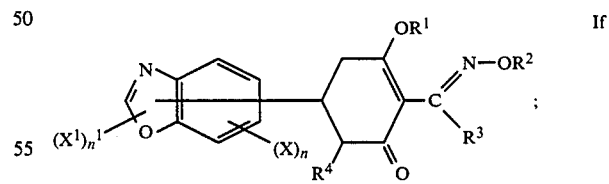

benzothiazole derivatives of formula Ig

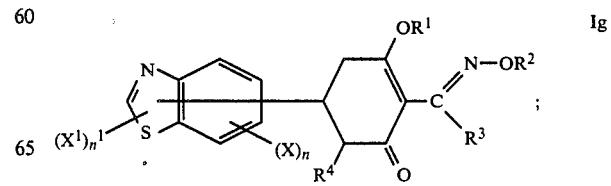

benzimidazole derivatives of formula Ih

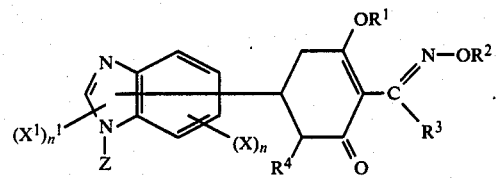

Preferred compounds of the invention include those compounds of formula I wherein:

A is selected from CH and N;

B is selected from oxygen, sulfur, $CH_2$ and the group N—Z wherein Z is selected from hydrogen and $C_1$ to $C_6$ alkyl;

X, which may be the same or different, and $X^1$, which may be the same or different, are independently selected from the group consisting of halogen, $C_1$ to $C_6$ alkyl, $C_1$ to $C_6$ haloalkyl, $C_1$ to $C_6$ alkoxy, $C_1$ to $C_6$ alkylthio, formyl, $C_2$ to $C_6$ alkanoyl, and the group of the formula $—C(R^7)=NR^8$ wherein $R^7$ is selected from hydrogen and $C_1$ to $C_5$ alkyl and $R^8$ is selected from hydroxy and $C_1$ to $C_6$ alkoxy;

$R^1$ is selected from the group consisting of: hydrogen; $C_2$ to $C_6$ alkanoyl; benzoyl and substituted benzoyl wherein the benzene ring is substituted with from one to three substituents selected from the group consisting of halgen, nitro, $C_1$ to $C_6$ alkyl and $C_1$ to $C_6$ alkoxy; benzenesulfonyl and substituted benzenesulfonyl wherein the benzene ring is substituted with from one to three substituents selected from the group consisting of halogen, nitro, $C_1$ to $C_6$ alkyl and $C_1$ $C_6$ alkoxy; and an inorganic or an organic cation selected from the alkali metals such as lithium, potassium and sodium, the alkaline earth metals such as magnesium, calcium and barium, the transition metals such as manganese, copper, zinc, iron, nickel, cobalt and silver, the ammonium ion and the tri- and tetra(alkyl)ammonium ions wherein alkyl is selected from $C_1$ to $C_6$ alkyl and $C_1$ to $C_6$ hydroxyalkyl;

$R^2$ is selected from the group consisting of $C_1$ to $C_6$ alkyl, $C_2$ to $C_6$ alkenyl, $C_2$ to $C_6$ alkynyl, $C_1$ to $C_6$ haloalkyl, $C_2$ to $C_6$ haloalkenyl and $C_2$ to $C_6$ haloalkynyl;

$R^3$ is selected from $C_1$ to $C_6$ alkyl;

$R^4$ is hydrogen;

n is zero or an integer selected from 1 to 4; and $n^1$ is zero or an integer selected from 1 to 3.

One more preferred group of compounds of the invention include those compounds of formula

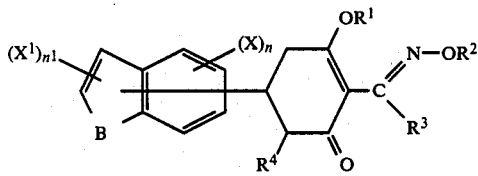

wherein

B is selected from oxygen and sulfur and N-Z wherein Z is selected from hydrogen and $C_1$ to $C_6$ alkyl;

X, which may be the same or different, and $X^1$, which may be the same or different, are independently selected from the group consisting of halogen, $C_1$ to $C_6$ alkyl, $C_1$ to $C_6$ alkoxy, $C_1$ to $C_6$ alkylthio and $C_2$ to $C_6$ alkanoyl;

$R^1$ is selected from the group consisting of hydrogen, benzoyl and the alkali metals;

$R^2$ is selected from the group consisting of $C_1$ to $C_6$ alkyl, $C_1$ to $C_6$ haloalkyl, $C_2$ to $C_6$ alkenyl and $C_2$ to $C_6$ alkynyl;

$R^3$ is selected from the group consisting of $C_1$ to $C_6$ alkyl;

$R^4$ is hydrogen;

n is zero or an integer selected from 1 to 4; and $n^1$ is zero or an integer selected from 1 and 2.

Another group of more preferred compounds of the present invention include those compounds of formula

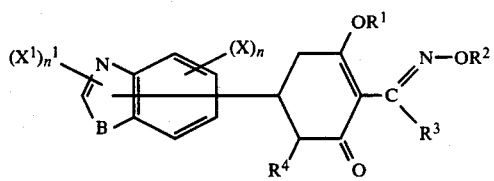

wherein:

B is selected from oxygen and sulfur;

X, which may be the same or different, and $X^1$, which may the the same or different, are independently selected from the group consisting of halogen, $C_1$ to $C_6$ alkyl, $C_1$ to $C_6$ alkoxy, $C_1$ to $C_6$ alkylthio and $C_2$ to $C_6$ alkanoyl;

$R^1$ is selected from the group consisting of hydrogen, benzoyl and the alkali metals;

$R^2$ is selected from the group consisting of $C_1$ to $C_6$ alkyl, $C_1$ to $C_6$ haloalkyl, $C_2$ to $C_6$ alkenyl and $C_2$ to $C_6$ alkynyl;

$R^3$ is selected from the group consisting of $C_1$ to $C_6$ alkyl;

$R^4$ is hydrogen;

n is zero or an integer selected from 1 to 4; and $n^1$ is zero or 1.

A group of even more preferred compounds of the invention include those compounds of formula

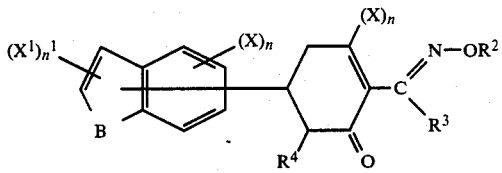

wherein:

B is selected from oxygen and sulfur;

X, which may be the same or different, and $X^1$, which may be the same or different, are independently selected from the group consisting of halogen and $C_1$ to $C_3$ alkyl;

$R^1$ is selected from the group consisting of hydrogen and the alkali metals;

$R^2$ is selected from the group consisting of $C_1$ to $C_3$ alkyl, $C_1$ to $C_3$ fluoroalkyl, allyl and propargyl;

$R^3$ is selected from the group consisting of $C_1$ to $C_3$ alkyl;

$R^4$ is hydrogen;

n is zero or an integer selected from 1 to 3; and $n^1$ is zero.

Another group of even more preferred compounds of the present invention include those compounds of formula

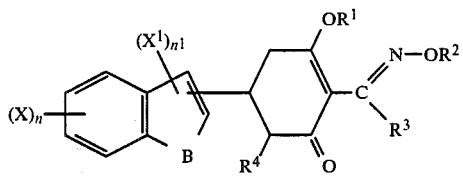

wherein:

B is the group N-Z wherein N is selected from hydrogen and $C_1$ to $C_3$ alkyl;

X, which may be the same or different, and $X^1$, which may be the same or different, are independently selected from the group consisting of halogen and $C_1$ to $C_3$ alkyl;

$R^1$ is selected from the group consisting of hydrogen and the alkali metals;

$R^2$ is selected from the group consisting of $C_1$ to $C_3$ alkyl, $C_1$ to $C_3$ fluoroalkyl, allyl and propargyl;

$R^3$ is selected from the group consisting of $C_1$ to $C_3$ alkyl;

$R^4$ is hydrogen;

n is zero or an integer selected from 1 to 4; and $n^1$ is zero or 1.

A further group of even more preferred compounds of the present invention include those compounds of formula

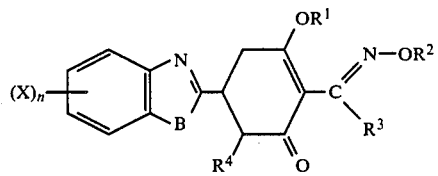

wherein:

B is selected from oxygen and sulfur;

X, which may be the same or different, are selected from the group consisting of halogen and $C_1$ to $C_3$ alkyl;

$R^1$ is selected from the group consisting of hydrogen and the alkali metals;

$R^2$ is selected from the group consisting of $C_1$ to $C_3$ alkyl, $C_1$ to $C_3$ fluoroalkyl, allyl and propargyl;

$R^3$ is selected from the group consisting of $C_1$ to $C_3$ alkyl;

$R^4$ is hydrogen; and n is zero or an integer selected from 1 to 4.

Particularly preferred values for X and $X^1$ include chlorine and methyl.

Particularly preferred values for $R^1$ include hydrogen and the alkali metals.

Particularly preferred values for $R^2$ include ethyl, fluoroethyl, allyl and propargyl.

Particularly preferred values for $R^3$ include ethyl and n-propyl.

Particularly preferred $R^4$ is hydrogen.

Specific examples of the compounds of the invention include those compounds detailed in Table 1 below.

TABLE 1

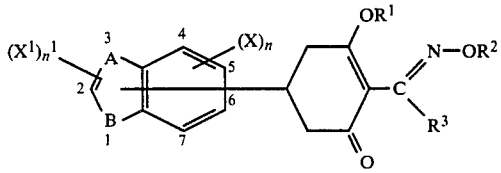

| Compound No | A | B | $(X)_n$, $(X^1)_{n1}$ | Link | $R^1$ | $R^2$ | $R^3$ |
|---|---|---|---|---|---|---|---|
| 11 | CH | S | H | 5 | H | $C_2H_5$ | $C_2H_5$ |
| 12 | CH | S | H | 6 | H | $C_2H_5$ | $CH_2CH_2CH_2$ |
| 13 | CH | S | H | 4 | H | $C_2H_5$ | $CH_2CH_2CH_3$ |
| 14 | CH | O | H | 5 | H | $C_2H_5$ | $CH_2CH_2CH_3$ |
| 15 | C | N | 1,3-$(CH_3)_2$ | 2 | H | $C_2H_5$ | $CH_2CH_2CH_3$ |
| 16 | C | N | 1,2-$(CH_3)_2$ | 3 | H | $C_2H_5$ | $CH_2CH_2CH_3$ |
| 17 | C | C | 1,1,3,4,5,6,7-$(CH_3)_7$ | 2 | H | $C_2H_5$ | $C_2H_5$ |
| 18 | CH | O | H | 2 | H | $C_2H_5$ | $CH_2CH_2CH_3$ |
| 19 | CH | O | 4,5,6-$(CH_3)_3$ | 7 | H | $C_2H_5$ | $CH_2CH_2CH_3$ |
| 20 | CH | O | 2-$CH_3CO$—4,5,6-$(CH_3)_3$ | 7 | H | $C_2H_5$ | $CH_2CH_2CH_3$ |
| 21 | CH | O | 7-Cl—4,5-$(CH_3)_2$ | 6 | H | $C_2H_5$ | $CH_2CH_2CH_3$ |
| 22 | CH | O | 5,6,7-$(CH_3)_3$ | 4 | H | $C_2H_5$ | $CH_2CH_2CH_3$ |
| 23 | CH | O | 4,6,7-$(CH_3)_3$ | 5 | H | $C_2H_5$ | $CH_2CH_2CH_3$ |
| 24 | C | N | 1,3-$(CH_3)_2$ | 2 | H | a | $CH_2CH_2CH_3$ |
| 25 | C | N | 1,3-$(CH_3)_2$ | 2 | H | b | $CH_2CH_2CH_3$ |
| 26 | C | N | 1,3-$(CH_3)_2$ | 2 | H | $CH_2CH_2F$ | $CH_2CH_2CH_3$ |
| 27 | C | N | 1,3-$(CH_3)_2$ | 2 | $Na^+$ | $C_2H_5$ | $CH_2CH_2CH_3$ |
| 28 | C | N | 1,3-$(CH_3)_2$ | 2 | H | c | $CH_2CH_2CH_3$ |
| 29 | N | S | H | 2 | H | $C_2H_5$ | $C_2H_5$ |

Code:
a = $CH_2CH=CH_2$
b = $CH_2C\equiv CH$
c = $COC_6H_5$

The compounds of the invention may be prepared by by a variety of methods and in a further aspect the invention provides methods for the preparation of compounds of formula I.

Conveniently the preparation of the compounds of the invention can be considered in three or four parts.

Part A involves the formation of a 5-arylcyclohexan-1,3-dione of formula IX. This reaction may be carried out in a two step process by:

(i) reacting, preferably in the presence of a base, an aldehyde derivative of formula V with acetone (IVa) or an acetone derivative of formula IVb to form a ketone derivative of formula VIa or VIb respectively; and reacting, preferably in the presence of a base, a ketone derivative of formula VIa with a malonic acid ester derivative of formula VIIa or a ketone derivative of formula VIb with a malonic acid ester of formula VIIb, to give an intermediate of formula VIIIa or VIIIb respectively which may be isolated or hydrolysed directly, preferably in the presence of an acid, to give a 5-arylcyclohexan-1,3-dione of formula IX, or reacting, preferably in the presence of a base, a ketone derivative of formula VIa with an alkanoic acid ester of formula VIIc to give a 5-arylcyclohexan-1,3-dione of formula IX;

(ii) reacting, preferably in the presence of a base, an aldehyde derivative of formula V with a malonic acid ester of formula VIIb to give an arylmethylidenemalonate derivative of formula VIc which is in turn reacted, preferably in the presence of a base, with an acetoacetic acid derivative of formula VIId to give an intermediate of formula VIIIc which may be isolated or hydrolysed directly, preferably in the presence of an acid, to give a 5-arylcyclohexan-1,3-dione of formula IX; or (iii) reacting, preferably in the presence of a base, an aldehyde derivative of formula V with an acetic acid ester of formula IVc to give a 2-arylalkenoate derivative of formula VId which is in turn reacted, preferably in the presence of a base, with an acetoacetic acid ester derivative of formula VIId to give an intermediate of formula VIIIa which may be isolated or hydrolysed directly, preferably in the presence of an acid, to give a 5-arylcyclohexan-1,3-dione of formula IX.

Part B involves the acylation of a compound of formula IX to give a 2-acyl-5-arylcyclohexan-1,3-dione of formula XIII. This reaction may be carried out by reacting a 5-arylcyclohexan-1,3-dione of formula IX with:

(iv) an acid anhydride of formula X in the presence of either an alkali metal salt of the corresponding acid of formula XI or an alkoxide salt of formula XII, wherein M is an alkali metal ion and R is $C_1$ to $C_6$ alkyl;

(v) an acid anhydride of formula X in the presence of the corresponding acid of formula XIV;

(vi) an acid halide of formula XV, wherein hal represents halogen, in the presence of a Lewis acid catalyst;

(vii) a mixture of an acid halide of formula XV and the corresponding acid of formula XIV; or (viii) with an alkali or alkaline earth metal hydride followed by reaction with an acid anhydride of formula X or an acid halide of formula XV.

Alternatively, this acylation reaction may be carried out by:

(ix) reacting a 5-arylcyclohexan-1,3-dione of formula IX with an acid halide of formula XV in the presence of pyridine to give an intermediate O-acyl derivative of formula XVI; and (x) reacting the intermediate of formula XVI with a Lewis acid catalyst;

(xi) reacting the intermediate of formula XVI with the acid of formula XIV; or (xii) reacting the intermediate of formula XVI with imidazole.

Part C involves the formation of a compound of the invention of formula I wherein $R^1$ is hydrogen, that is a compound of formula II. This reaction may be carried out either by reacting a 2-acyl-5-arylcyclohexan-1,3-dione of formula XIII with:

(xiii) an alkoxyamine derivative of formula XVII; or (xiv) hydroxylamine to give an intermediate oxime derivative of formula XVIII and reacting that intermediate oxime derivative of formula XVIII with an alkylating agent of formula XIX wherein L is a leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, methanesulfonate and trifluoromethanesulfonate.

Part D involves the formation of a compound of the invention of formula I wherein $R^1$ is a substitutent other than hydrogen.

Compounds of the invention of formula I, wherein $R^1$ forms an ether, acyl or sulfonyl derivative of a compound of formula II, may be prepared from the corresponding compounds of the invention of formula II by reacting with an etherification, acylation or sulfonylation reagent of formula XX.

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, as hereinbefore defined, which process comprises:

reacting 2-acyl-5-(aryl)cyclohexane-1,3-dione derivative of formula XIII with an alkoxyamine derivative of formula XVII to give a compound of the invention of formula II or reacting the 2-acyl-5-(aryl)cyclohexane-1,3-dione derivative of formula XIII with hydroxylamine and alkylating the oxime intermediate of formula XVIII with an alkylating agent of formula XIX, wherein L is a leaving group, to give a compound of the invention of formula II; and optionally reacting the compound of the invention of formula II with a compound of formula XX, wherein L is a leaving group, to give a compound of the invention of formula I.

Certain of the intermediate compounds of formulae V, VIa, VIb, VIc, VId, VIIIa, VIIIb, VIIIc, IX, XIII, XVI and XVIII are novel compounds and therefore in further embodiments the invention provides novel compounds of formulae V, VIa, VIb, VIc, VId, VIIIa, VIIIb, VIIIc, IX, XIII, XVI and XVIII and processes for the preparation thereof.

The structures of the compounds described above are detailed on the following pages wherein φ represents the group

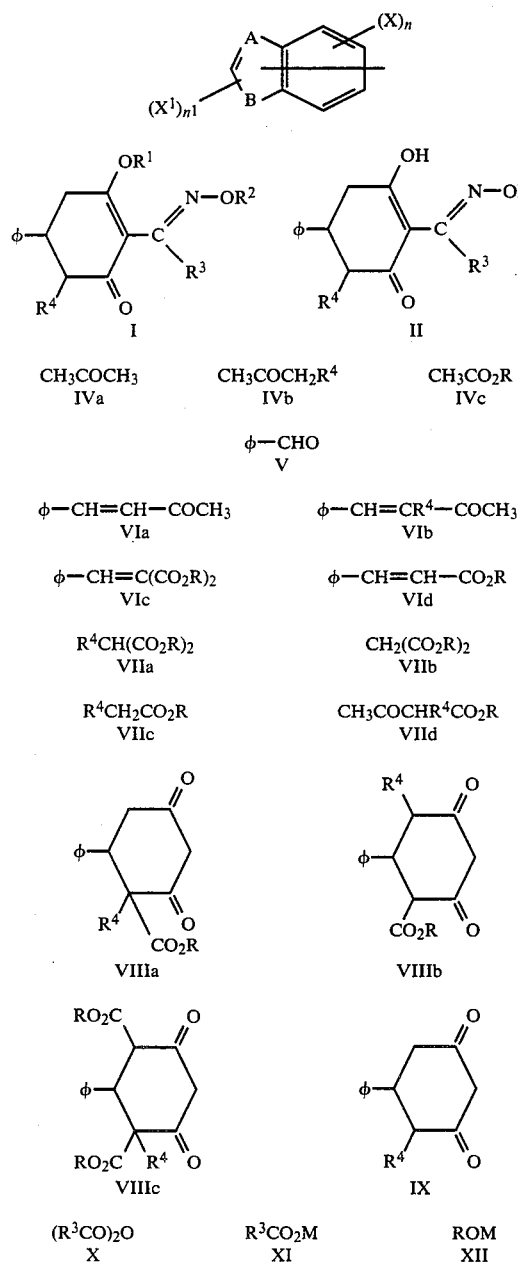

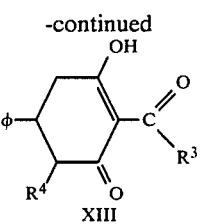

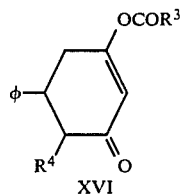

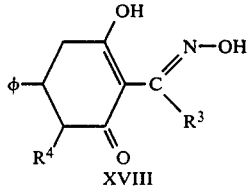

Certain of the intermediate compounds of formulae V, VI, VIII, IX, X, XII, XXI, XIII, XVI and XVIII are novel compounds and therefore as a further embodiment the invention provides novel compounds of formulae V, VI, VIII, IX, X, XII, XXI, XIII, XVI and XVIII, wherein the substituents are as hereinbefore defined, and processes for the preparation thereof.

The compounds of formula I are active as herbicides and therefore, in a further aspect the invention provides a proces for severely damaging or killing unwanted plants which process comprises applying to the plants, or to the growth medium of the plants, an effective amount of a compound of formula I as hereinbefore defined.

Generally speaking the compounds of formula I are herbicidally effective against a variety of plants. However, certain of the compounds of the invention are selectively active against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to control monocotyledonous weeds in cultivated crops, especially wild grasses in cereal crops. Certain of such compounds of the invention are especially useful in the control of wild grasses such as wild oats and rye grass in crops of cultivated monocotyledonous plants such as wheat and other varieties of cereals.

Accordingly, in yet a further aspect the invention provides a process for controlling monocotyledonous weeds in cultivated crops, especially wild grasses in cereal crops such as wheat, which process comprises applying to the crop, or to the growth medium of the crop a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an agriculturally acceptable carrier therefor.

Certain of the compounds of formula I exhibit useful plant growth regulating activity. For example, while compounds of formula I are selectively active herbicides against wild grasses in crops of cultivated plants at some rates of application they exhibit plant growth regulating effects in said crops.

Plant growth regulating effects may be manifested in a number of ways. For example, suppression of apical dominance, stimulation of auxiliary bud growth, stimulation or early flowering and seed formation, enhancement of flowering and increase in seed yield, stem thickening, stem shortening and tillering. Plant growth regulating effects shown by compounds of the invention may include, for example, tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an agriculturally acceptable carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomerating techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acids, the di- and triisopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersions of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compostions are generally prepared by mixing concentrated compositions with water. Suitable concentrated compositions include emulsion concentrates, pastes, oil dispersions, aqueous suspensions and wettable powders. The concentrates are usually required to withstand lstorage for prolonged periods and after such storage to be capable of dilution with water to form aqueous preparations which remain homogeneous for a sufficient time to enable them to be applied by conventional spray equipment. The concentrate conveniently contain from 20 to 99%, preferably 20 to 60%, by weight of active ingredient.

Emulsion or emulsifiable concentrates are conveniently prepared by dissolving the active ingredient in an organic solvent containing one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active agent and preferably at least one suspending agent. Suitable suspending agents include: hydrophilic colloids such as, for example, poly(N-vinylpyrrolidone), sodium carboxymethylcellulose and the vegetable gums, gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectate is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Example of useful complementary herbicides include:

A. benzo-2,1,3-thiadiazin-4-one-2,2-dioxides such as 3-isopropylbenzo-2,1,3-thiadiazin-4-one-2,2-dioxide (common name bentazon);
B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name 2,4-D), 4-(2,4-dichlorophenoxy)-butyric acid (common name 2,4-DB), 2-(4-chloro-2-methylphenoxy)propionic acid (common name mecoprop), and their derivatives (eg salts, esters, amides and the like);
C. 3-[4-(4-halophenoxy)phenyl]-1,1-dialkylureas such as 3-[4-(4-chlorophenoxy)phenyl]-1,1-dimethylurea (common name chloroxuron);
D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;
E. dinitroaniline herbicides such as N',N'-diethyl-2,6-dinitro-4-trifluoromethyl-m-phenylenediamine (common name dinitramine), 2,6-dinitro-N,N-dipropyl-4- trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diruon) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)-carbamate (common name phenmedipham) and 3-[(ethoxycarbonylamino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine). 2-chloro-4,6-di(ethylamino)-1,3,5-triazine (common name simazine) and 2-azido-4-(isopropylamino)-6-methylthio-1,3,5-triazine (common name aziproptryne);

K. 1-alkoxy-2-alkyl-3-phenylurea herbicides such a 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiolcarbamate herbicides such as S-propyl dipropylthiocarbamate (common name verolate);

M. 1,2,4-triazin-5-one herbicides such as 4-amino-4,5-dihydro-3-methyl-6-phenyl-1,2,4-triazine-5-one (common name metamitron) and 4-amino-6-tert-butyl 4,5-dihydro-3-methylthio-1,3,4-triazine-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

O. anilide herbicides such as N-butoxymethyl-α-chloro-2',6'-diethylacetanilide (common name butachlor), the corresponding N-methoxy compound (common name alachlor), the corresponding N-isopropyl compound (common name propachlor) and 3',4'-dichloropropionanilide (common name propanil);

P. dihalobenzonitrile herbicides such as 2,6-dichalorobenzonitrile (common name dichlobenil), 3,5-dibromo-4-hydroxybenzonitrile (common name bromoxynil) and 3,5-diiodo-4-hydroxybenzonitrile (common name ioxynil);

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189); and T. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

U. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

V. organoarsenical herbicides such as monosodium methanearsonate (common name MSMA); and W. amino acid herbicides such as N-(phosphonomethyl)glycine (common name glyphosate) and its salts and esters.

The invention is now illustrated by but in no way limited to the following Examples.

EXAMPLE 1

This example details the preparation of carboxaldehydes of formula V which were used in the preparation of compounds of the invention of formula I.

(a) Benzo[b]thiophene-5-carboxaldehyde was prepared according to the procedure described in Nippon Kagaku Zasshi, 87, 186 (1966) [Chem. Abstr., 65 15301 g (1966)].

(b) Benzo[b]thiophene-6-carboxaldehyde. A mixture of 6-bromobenzo[b]thiophene [9.6 g; prepared according to Nippon Kagaku Zasshi, 88, 758 (1967): Chem. Abstr., 69, 59018q (1968)], magnesium (1.64 g), and 1,2-dibromoethane (4.23 g) in anhydrous diethyl ether (90 ml) was stirred and gently heated for 3 hr. N-formylpiperidine (5.09 g) in anhydrous diethyl ether (15 ml) was added to the cooled mixture which was subsequently allowed to stand for 12 hr. the mixture was poured into a dilute hydrochloric acid solution. the dried (MgSO$_4$) ether extract was evaporated and the residue was purified by column chromatography over silica gel with chloroform/hexane (1:8 v/v) elution to give benzo[b]thiophene-6-carboxaldehyde as yellow oil. Pmr spectrum (CDCl$_3$; δ in ppm): 7.36 (1H, d); 7.68 (1H, d); 7.84 (2H, s); 8.16 (1H, s); 10.04 (1H, s).

(c) Benzo[b]thiophene-4-carboxaldehyde was prepared from 4-bromobenzo[b]thiopehen following essentially the same procedure as that described in (b) above. Benzo[b]thiophene-4-carboxaldehyde was obtained as a yellow oil. Pmr spectrum (CDCl$_3$; δ in ppm): 7.44 (1H, t); 7.64 (1H, d); 7.80 (1H, d of d); 8.04 (1H, m); 8.28 (1H, d of d); 10.16 (1H, s).

(d) benzo[b]furan-5-carboxaldehyde was prepared from 5-bromobenzo[b]furan (prepared from 4-bromophenol and bromoacetaldehyde diethyl acetal by the general method described in J. Chem. Soc. Perkin 1, 1972, 556) following essentially the same procedure as that described in (b) above. Benzo[b]furan-5-carboxaldehyde was obtained as an oil. Pmr spectrum (CDCl$_3$; δ in ppm): 6.90 (1H, d); 7.55–7.93 (3H, m); 8.15 (1H, d); 10.08 (1H, s).

(e) 1,1,3,4,5,6,7-Heptamethylindene-2-carboxaldehyde. Titanium tetrachloride (14.0 g) was added dropwise to a solution of 1,1,3,4,5,6,7-heptamethylindene (10.0 g) in dichloroethane (200 ml) at a temperature below 5° C. Dichloromethyl methyl ether (4.4 g) was added and the reaction mixture was warmed to room temperature. After 30 minutes at room temperature the reaction mixture was heated under reflux for a period of 1 hour. After cooling, the mixture was poured into an ice-water mixture, hydrochloric acid was added and the aqueous mixture was extracted with dichloromethane. The organic phase was separated, washed with water, dried over anhydrous sodium sulfate and the solvent was evaporated. The residue was purified by column chromatography over silica gel (eluant dichloromethane) to give 1,1,3,4,5,6,7-heptamethylindene-2-carboxaldehyde as a crystalline solid, mp 176° C. Proton magnetic resonance spectrum (CDCl$_3$; δ in ppm): 1.51 (6H, s); 2.27 (6H, s); 2.43 (3H, s); 2.57 (3H, s); 2.70 (3H, s); 10.20 (1H, s).

(f) Benzo[b]furan-2-carboxaldehyde was prepared according to the method described in French Patent publication No. 1 537 206 (Chem. Abstr., 1969, 71, 61198h).

(g) 1,3-Dimethylindole-2-carboxaldehyde was prepared by Vilsmeier-Haak formylation of 1,3-dimethylindole following the procedure described in J. Heterocyclic Chem., 1981, 18, 1275.

(h) 1,2-Dimethylindole-3-carboxaldehyde (mp 129° C.) was prepared from 1,2-dimethylindole following essentially the same procedure as that used for the preparation of 1,3-dimethylindole-2-carboxaldehyde referred to in (g) above.

(i) Benzothiazole-2-carboxaldehyde was prepared according to the method described in Chem. Ber., 1956, 89, 1893 (Chem. Abstr. 1957, 51, 12075b).

EXAMPLE 2

The 1-(aryl or heteroaryl)but-1-en-3-one derivatives of formula VIa used in the preparation of compounds of the invention of formula I were prepared from the appropriate carboxaldehydes of formula V by one of the following methods:

(a) An aqueous solution of 10% sodium hydroxide (1 ml) was added dropwise to a solution of benzo[b]thiophene-5-carboxaldehyde (7.0 g) in acetone (15 ml) and water (5 ml), the temperature of the reaction mixture being maintained below 30° C. during the addition. On completion of the reaction (ca 3 hrs) the mixture was poured into water. The dried (MgSO$_4$) dichloromethane extract was evaporated to give 1-(benzo[b]thien-5-yl)but-1-en-3-one as a yellow solid, mp 75° C.

(b) A solution of benzo[b]furan-2-carboxaldehyde (3.3 g) and 1-triphenylphosphoranylidene-2-propanone (1.2 equivalents) in dimethyl sulfoxide (180 ml) was stirred at a temperature of 35° C. for a period of 30 minutes. The cooled mixture was poured into water and the aqueous mixture was extracted with diethyl ether. The solvent was evaporated from the dried (MgSO$_4$) fraction and the residue was purified by column chromatography over silica gel (dichloromethane elution) to give 1-(benzo[b]furan-2-yl)but-1-en-3-one (3.0 g) as an orange solid, mp 100°–101° C.

(c)

(i) A 40% aqueous formaldehyde solution (16.3 ml, 218 mmol) was added dropwise to a mixture of 3,4,5-trimethylphenol (29.6 g, 218 mmol) and a 26% aqueous dimethylamine solution (38 ml). The mixture was allowed to stand at room temperature overnight and was then poured into a dilute hydrochloric acid solution (15%, 200 ml). The mixture was extracted with ether and the aqueous acidic fraction was carefully neutralized with a 20% sodium hydroxide solution. The dried (Na$_2$SO$_4$) ether extract was evaporated to give 2-(dimethylaminoethyl)-3,4,5-trimethylphenol (31.9 g, 76%) as a white solid, mp 72° C.

(ii) A mixture of 2-(dimethylaminomethyl)-3,4,5-trimethylphenol (31.85 g, 165 mmol) and iodomethane (31 ml, 495 mmol) in dichloromethane (250 ml) was allowed to stand at room temperature for 72 hours. The methiodide was filtered off and used without further purification.

(iii) A solution of dimethylsulfoxonium methylide was prepared by adding trimethylsulfoxonium iodide (36.3 g, 165 mmol) to a well-stirred mixture of sodium hydride (165 mmol) and anhydrous dimethylsulfoxide (100 ml) at room temperature under nitrogen. 2-(Dimethylaminomethyl)-3,4,5-trimethylphenol methiodide (165 mmol) was added and the mixture was stirred at room temperature for 24 hr. The mixture was poured onto an ice-water mixture which was then extracted with dichloromethane. Evaporation of the dried (Na$_2$SO$_4$) organic extract followed by column chromatography of the residue over silica with dichloromethane elution gave 2,3-dihydro-4,5,6-trimethylbenzo[b]furan (7.84 g, 29%) as a pale yellow oil.

(iv) 2,3-Dihydro-4,5,6-trimethylbenzo[b]furan-7-carboxaldehyde was prepared from 2,3-dihydro-4,5,6-trimethylbenzo[b]furan following the general method of Organic Synthesis, Coll. vol. v, 49 and was obtained as a yellow solid, mp 90° C.

(v) 1-(2,3-Dihydro-4,5,6-trimethylbenzo[b]furan-7-yl)but-1-en-3-one was prepared from 2,3-dihydro-4,5,6-trimethylbenzo[b]furan-7-carboxaldehyde and acetone following essentially the same procedure as that described in Example 2 part (a), and was obtained as a pale brown solid, mp 116° C.

(vi) 2,3-Dichloro-5,6-dicyano-1,4-benzoquinone (5.0 g) was added to a solution of 1-(4,5,6-trimethyl-2,3-dihydrobenzo[b]furan-7-yl)-but-1-en-3-one (5.0 g) in toluene (100 ml) and the mixture was stirred at room temperature for a period of 24 hours. The solvent was evaporated by distillation under reduced pressure and the residue was purified by column chromatography over silica gel with dichloromethane elution to give 1-(4,5,6-trimethylbenzo[b]furan-7-yl)but-1-en-3-one (4.2 g; 85%) as a pale yellow solid, mp 99° C.

(d) 1-(7-Chloro-4,5-dimethylbenzo[b]furan-6-yl)but-1-en-3-one was prepared from 2-chloro-4,5-dimethylphenol following essentially the same procedure as that described in part (c) above.

(e) 1-(5,6,7-Trimethylbenzo[b]furan-4-yl)but-1-en-3-one was prepared from 2,3,4-trimethylphenol following essentially the same procedure as that described in part (c) above.

(f) 1-(4,6,7-Trimethylbenzo[b]furan-5-yl)but-1-en-3-one was prepared from 2,3,5-trimethylphenol following essentially the same procedure as that described in part (c) above.

The specific method used to prepare each of the 1-(aryl or heteroaryl)but-1-en-3-one derivatives of formula VIa is given in Example 5, Table 5 and physical and spectroscopic data for each of the derivatives is detailed in Table 2 below.

TABLE 2

$$(X^1)_n^1 \underset{R}{\overset{A}{\diagdown}} \underset{}{\overset{(X)_n}{\diagup}} -CH=CH-COCH_3 \quad VIa$$

| Intermediate of Formula VIa Used in the Preparation of Compound No(s) | Appearance | Proton Chemical Shift (δ in ppm; CDCl₃) |
|---|---|---|
| 11 | Yellow solid, mp 75° C. | — |
| 12 | White solid, mp 80° C. | — |
| 14 | White solid, mp 70° C. | — |
| 15 and 24–28 | Pale Yellow solid, mp 202–205° C. | — |
| 16 | Orange solid, mp 82° C. | — |
| 17 | Oil | 1.48(6H, s); 2.26 (6H, s); 2.37(3H, s); 2.43(3H, s); 2.49(3H, s); 2.56 (3H, s); 6.35(1H, d; 7.68(1H, d). |
| 18 | Orange solid, mp 100–101° C. | — |
| 19 | Pale yellow solid, mp 99° C. | — |
| 21 | Yellow solid, mp 72° C. | — |
| 22 | Orange oil | 2.30(3H, s); 2.38 (3H, s); 2.44(3H, s); 2.49(3H, s); 6.66(1H, d); 6.92 (1H, d); 7.62(1H, d); 8.02(1H, d). |
| 23 | Yellow solid, mp 83° C. | — |
| 29 | Yellow solid, mp 89° C. | — |

EXAMPLE 3

The 2-acyl-3-hydroxy-5-(aryl or heteroaryl)-cyclohex-2-en-1-ones of formula XIII used in the preparation of the compounds of the invention of formula I were prepared from the appropriate 1-(aryl or heteroaryl)but-1-en-3-one derivatives of formula VIa by one of the following methods:

(a)

(i) Diethyl malonate (7.16 g) was added to a solution of sodium metal (1 equiv) in anhydrous absolute ethanol (40 ml). 1-(Benzo[b]thien-5-yl)but-1-en-3-one (8.7 g) was added to the solution and the mixture was heated under reflux for 2 hr. An aqueous solution of potassium hydroxide (5.3 g in 50 ml water) was added and the mixture was heated under reflux for a further 5 hr. The hot mixture was acidified by dropwise addition of a dilute aqueous hydrochloric acid solution. After cooling, the product was filtered off and dried by azeotropic distillation with toluene to give 3-hydroxy-5-(benzo[b]thien-5-yl)cyclohex-2-en-1-one as a yellow solid, mp 192° C.

(ii) Sodium hydride (0.27 g) and 3-hydroxy-5-(benzo[b]thien-5-yl)cyclohex-2-en-1-one (2.5 g) were stirred in anhydrous dimethylformamide (25 ml) at 60° C. under nitrogen for 20 min. Propionic anhydride (1.5 ml) was added and the mixture was stirred and heated at 110° C. for 4 hr. The cooled mixture was poured into an ice/dilute hydrochloric acid solution, and the resulting mixture was extracted with diethyl ether. After evaporation of the dried (MgSO₄) organic extract the residue was purified by column chromatography over silica gel with chloroform/hexane (1:1 v/v) elution to give 3-hydroxy-5-(benzo[b]thien-5-yl)-2-propionylcyclohex-2-en-1-one as a yellow solid, mp 134° C. Pmr spectrum (CDCl₃; δ in ppm): 1.20 (3H, t); 2.72–3.04 (4H, m); 3.04–3.24 (2H, q); 3.32–3.60 (1H, m); 7.12–7.28 (2H, m); 7.44 (1H, d); 7.60 (1H, s); 7.80 (1H, d); 18.16 (1H, s).

(b) 1-(Benzo[b]furan-5-yl)but-1-en3-one (1.3 g) and sodium diethyl malonate (1.1 equiv) were heated at reflux in absolute ethanol (40 ml) for 4 hr. The solvent was evaporated and the residue was thoroughly dried (100° C.; <0.1 mmHg). The residue was dissolved in anhydrous dimethylformamide (40 ml) heated to 60° C. under nitrogen. n-Butyric anhydride (1.1 equiv) was added and the mixture was heated and stirred at 100° C. for 20 min. The solvent was evaporated by reduced pressure distillation and the residue was boiled with an aqueous potassium hydroxide solution (3 equiv. 40 ml) for 4 hr. The hot solution was acidified by slow addition of dilute hydrochloric acid. The cooled mixture was extracted with ethyl acetate. After drying (MgSO₄), the organic extract was evaporated and the residue was purified by column chromatography over silica gel with dichloromethane elution to give 3-hydroxy-5-(benzo[b]furan-5-yl)-2-butyrylcyclohex-2-en-1-one as a white solid, mp 71° C. Pmr spectrum (CDCl₃; δ in ppm): 1.00 (3H, t); ca 1.71 (2H, m); 2.70–3.7 (7H, m); (6.74 (1H, m); 7.10–7.56 (3H, m); 7.62 (1H, d); 18.30 (1H, s).

(c) Dimethyl malonate (1.3 g) was added to a solution of sodium metal (230 mg) in methanol (50 ml). A solution of 1-(4,5,6-trimethylbenzo[b]furan-7-yl)-but-1-en-3-one (1.5 g) in methanol (20 ml) was added and the mixture was heated at reflux with stirring for 2.5 hrs. The solvent was evaporated by distillation under reduced pressure and the residue was thoroughly dried. n-Butyryl chloride (250 mg) was added to a suspension of the residue in toluene (50 ml) and the mixture was stirred and heated at 80° C. for 40 min. 4-N,N-Dimethylaminopyridine (160 mg) was added and the mixture was stirred and heated at 80° C. for a further 4 hrs. On cooling the solution was washed successively with 10% aqueous hydrochloric acid and water. The dried (Na₂SO₄) organic fraction was evaporated by distillation under reduced pressure and the residue was heated at reflux with a 5% aqueous potassium hydroxide solution (150 ml) for 4 hrs. The cooled mixture was extracted with ether and the aqueous fraction was collected and was heated to 60° C. The solution was acidified by the dropwise addition of 50% aqueous hydrochloric acid, and after cooling the mixture was extracted with dichloromethane. The dried (Na₂SO₄) organic fraction was evaporated and the residue was purified by column chromatography over silica with dichloromethane elution to give 3-hydroxy-5-(4,5,6-trimethylbenzo[b]furan-7-yl)-2-butyryl cyclohex-2-en-1-one (1.0 g) as a white solid, mp 130° C. Pmr spectrum (CDCl₃; δ in ppm): 1.01 (3H, t); 1.70 (2H, m); 2.30 (3H, s); 2.36 (3H, s); 2.44 (3H, s); 2.4–4.0 (7H, m); 6.79 (1H, d); 7.56 (1H, d); 18.47 (1H, s).

The specific method used to prepare each of the 2-acyl-3-hydroxy-5-(aryl or heteroaryl)cyclohex-2-en-1-one derivative of formula XIII is given in Example 5, Table 5. Physical and spectroscopic data for each of the isolated 5-(aryl or heteroaryl)cyclohexan-1,3-dione derivatives of formula IX are given in Table 3 below and physical and spectroscopic data for each of the 2acyl-3-hydroxy-5-(aryl or heteroaryl)cyclohex-2-en-1-one derivatives of formula XIII are given in Table Table 4 below.

TABLE 3

IX (structure shown: (X¹)$_{n1}$-A-B-aryl-cyclohexane-1,3-dione with R⁴)

| Intermediate of Formula IX Used in the Preparation of Compound No(s) | Appearance | Proton Chemical Shift ($\delta$ in ppm; CDCl$_3$) |
|---|---|---|
| 11 | Yellow solid, mp 192° C. | — |
| 12 | White solid, mp 164° C. | — |
| 13 | White solid, mp 210° C. | — |
| 15 and 24 to 28 | Pale yellow solid mp 202–205° C. | — |
| 16 | Pale pink solid, mp 190–195° C. | — |
| 17 | Pale yellow solid | 1.19(6H, s); 2.09 (6H, s); 2.26(6H, s); 2.37(3H, s); 2.50–4.30(5H, m); 5.26(1H, s); 11.0–12.0(1H, broad s). |

TABLE 4

XIII (structure shown: (X¹)$_{n1}$-A-B-aryl-cyclohexenone with OH, C(=O)R³, R⁴)

| Intermediate of Formula XIII Used in the Preparation of Compound No(s) | Appearancee | Proton Chemical Shift ($\delta$ in ppm; CDCl$_3$) |
|---|---|---|
| 11 | Yellow solid, mp 134° C. | See Example 3, (a) (ii) |
| 12 | White solid, mp 117° C. | 1.00(3H,t); 2.52–2.88(2H,m); 2.64–3.12(6H,m); 3.24–3.60(1H,m); 7.12–7.36(3H,m); 7.64(1H, s); 7.70(1H,d); 18.24(1H,s). |
| 13 | Colourless oil | 0.98(3H,t); 1.44–1.84(2H,m); 2.68–3.12(6H,m); 3.74–4.04(1H,m); 7.04–7.48(4H,m); 7.72(1H, d); 18.28(1H,s). |
| 14 | White solid, mp 71° C. | See Example 3, (b) |
| 15 | Pale orange oil | 1.02(3H,t); 1.68 (2H,m); 2.37(3H,s); 2.5–3.7(7H,m); 3.66 (3H,s); 7.0–7.6(4H, m,); 18.32(1H,s). |
| 16 | Orange oil | 1.01(3H,t); 1.71 (2H,m); 2.34(3H,s); 2.4–3.7(7H,m); 3.63 (3H,s); 6.9–7.6(4H, m); 18.22(1H,s). |
| 17 | Low mp solid | 1.03(3H,t); 1.34 (6H,s); 1.67(2H,m); 2.10–3.45(7H,m); 2.24(6H,s); 2.38 (6H,s); 2.49(3H,s); 18.28(1H,s). |
| 18 | Pale yellow solid, mp 129–130° C. | 0.97(3H,t); 1.67 (2H,m); 2.8–3.8(7H, m); 6.46(1H,s); 7.12–7.58(4H,m); 18.33(1H,s). |
| 19 | White solid, 130° C. | See Example 3, (c) |
| 21 | Pale yellow oil | 1.03(3H,t); 1.69 (2H,m); 2.37(3H,s); 2.45(3H,s); 2.4–4.2 (7H,m); 6.79(1H,d); 7.63(1H,d); 18.35 (1H,d). |
| 22 | Pale yellow oil | 1.02(3H,t); 1.72 (2H,m); 2.3l(3H, s); 2.34(3H,s); 2.46(3H,s); 2.4–4.1(7H,m); 6.80 (1H,d); 7.57(1H,d); 18.35(1H,d). |
| 23 | Pale yellow solid, mp 119° C. | 1.01(3H,t); 1.72 (2H,m); 2.42(6H, s); 2.55(3H,s); 2.4–4.2(7H,m); 6.74 (1H,d); 7.55(1H,d); 18.40(1H,d). |
| 29 | Yellow solid | 1.22(3H,t); 2.89–3.37(6H,m); 3.69–4.08(1H,m); 7.32–8.10(4H,m); 18.21 (1H,s). |

EXAMPLE 4

The compounds of the invention of formula I were prepared from the appropriate 2-acyl-3-hydroxy-5-(aryl or heteroaryl)cyclohex-2-en-1-one of formula XIII or another compound of the invention of formula I by one of the following methods:

(a) A solution of sodium hydroxide (0.15 g) in water (2 ml) and then ethoxyamine hydrochloride (0.37 g) were added to a solution of 3-hydroxy-5-(benzo[b]thien-5-yl)-2-propionylcyclohex-2-en-1-one (1.05 g) in ethanol/dimethylformamide (5:2 v/v; (70 ml). The mixture was stirred at room temperature for 12 hr, and was subsequently poured into water. the dried (MgSO$_4$) diethyl ether extract was evaporated to give 2-[1-(ethoxyimino)propyl]-3-hydroxy-5-(benzo[b]thien-4-yl)cyclohex-2-en-1-one as a white solid, mp 76° C.

(b) A mixture of 3-hydroxy-5-(benzo[b]furan-2-yl)-2-butyryl cyclohex-2-en-1-one (1.0 g), ethoxyamine hydrochloride (0.36 g), sodium acetate (0.3 g) and ethanol (100 ml) were stirred at room temperature for 12 hr. The mixture was poured into a very dilute aqueous hydrochloric acid solution which was then extracted with ether. Evaporation of the dried (MgSO4) organic fraction and purification of the residue by column chromatography over silica with dichloromethane elution gave 2-[1-(ethoxyimino)-butyl]-3-hydroxy-5-(benzo[b]furan-2-yl)cyclohex-2-en-1-one as a yellow solid, mp 70° C.

(c) 2-[1-(Allyloxyimino)butyl]-5-(1,3-dimethylindol-3-hydroxycyclohex-2-en-1-one, 5-(1,3-dimethylindol-2-yl)-3-hydroxy-2-[1-(propargyloxyimino)-butyl]cyclohex-2-en-1-one and 5-(1,3-dimethylindol-2-yl)-2-[1-(2-fluoroethoxyimino)-butyl]-3-hydroxycyclohex-2-en-1-one were prepared from 2-butyryl-3-hydroxy-5-(1,3-dimethylindol-2-yl)cyclohex-2-en-1-one and the appropriate hydroxylamine derivative following essentially the same procedure as that described in Example 4 part (b).

(d) 5-(2-Acetyl-4,5,6-trimethylbenzo[b]furan-7-yl)-2-[1-(ethoxyimino)butyl]-3-hydroxycyclohex-2-en-1-one (20). 2-[1-(Ethoxyimino)butyl]-3-hydroxy-5-(4,5,6-trimethylbenzo[b]furan-7-yl)cyclohex-2-en-1-one (400 mg) was added to a suspension of aluminium trichloride (400 mg) in 1,2-dichloroethane (5 ml). The mixture was stirred at 0° C. for 40 min and acetyl chloride (100 mg) was added. After stirring a further 30 min at 0° C. and at room temperature for 1 hr the mixture was poured onto ice 50% aqueous hydrochloric acid (200 ml). The mixture was vigorously stirred for 30 min and was then extracted with dichloromethane. Evaporation of the dried (Na2SO4) organic fraction and purification of the residue by column chromatography over silica with dichloromethane elution gave 5-(2-acetyl-4,5,6-trimethylbenzo[b]furan-7-yl)-2-[1-(ethoxyimino)butyl]-3-hydroxycyclohex-2-en-1-one as a yellow solid, mp 154° C.

(e) 2-[1-(Ethoxyimino)butyl]-5-(1,3-dimethylindol-2-yl)-3-hydroxycyclohex-2-en-1-one sodium salt (27). A mixture of 2-[1-(ethoxyimino)butyl]-5-(1,3-dimethylindol-2-yl)-3-hydroxycyclohex-2-en-1-one (0.9 g), aqueous sodium hydroxide (1 equiv; 2 ml) and toluene (60 ml) was evaporated by distillation under reduced pressure. Toluene (60 ml) was added to the residue and the mixture was evaporated by distillation under reduced pressure. The residue was washed with a little ether leaving 2-[1-(ethoxyimino)butyl]-5-(1,3-dimethylindol-2-yl)-3-hydroxycyclohex-2-en-1-one sodium salt as a pale yellow solid, mp > 185° C. (dec.).

(f) 3-Benzoyloxy-2-[1-(ethoxyimino)butyl]-5-(1,3-dimethylindol-2-yl)cyclohex-2-en-1-one (28). A slight excess of benzoyl chloride was added to a suspension of 2-[1-(ethoxyimino)butyl]-5-(1,3-dimethylindol-2-yl)-3-hydroxycyclohex-2-en-1-one sodium salt (400 mg) in acetone (20 ml) and the mixture was stirred at room temperature for 1 hr. The solvent was evaporated under reduced pressure and the residue was shaken with water and dichloromethane. The dried (Na2SO4) organic fraction was evaporated and the residue was purified by column chromatography over silica with dichloromethane elution to give 3-benzoyloxy-2-[1-(ethoxyimino)-butyl]-5-(1,3-dimethylindol-2-yl)cyclohex-2-en-1-one as a pale yellow oil.

EXAMPLE 5

The specific method employed for the preparation of each of the 1-(aryl or heteroaryl)but-1-en-3-one derivatives of formula VIa (Example 2), the 5-(aryl or heteroaryl)-3-hydroxy cyclohex-2-en-1-one derivatives of formula IX (Example 3) and/or the 2-acyl-5-(aryl or heteroaryl)-3-hydroxycyclohex-2-en-1-one derivatives of formula XIII (Example 3) used as intermediates in the preparation of the compounds of the invention of formula I are listed in Table 5 below together with the specific Method employed for the preparation of the compounds of the invention of formula I (Example 4).

Each of the compounds of the invention of formula I were characterized by proton nuclear magnetic resonance spectroscopy and physical data and spectroscopic data are recorded in Table 6 below.

TABLE 5

| | Method of Preparation of Compounds of Formulae: | | |
|---|---|---|---|
| Compound No | VIa Example 2 Method | IX and XIII Example 3 Method | I Example 4 Method |
| 11 | a | a | a |
| 12 | a | a | a |
| 13 | a | a | a |
| 14 | a | b | a |
| 15 | a | a | a |
| 16 | a | a | a |
| 17 | a | a | a |
| 18 | b | b | b |
| 19 | c | c | b |
| 20 | — | — | d |
| 21 | d | c | b |
| 22 | e | c | b |
| 23 | f | c | b |
| 24 | a | a | c |
| 25 | a | a | c |
| 26 | a | a | c |
| 27 | a | a | e |
| 28 | a | a | f |
| 29 | b | c | b |

TABLE 6

| Compound No | Appearance | Proton Chemical Shift (CDCl3; δ in ppm) |
|---|---|---|
| 11 | White solid, mp 76° C. | 1.18(3H,t); 1.30(3H,t); 2.68–2.88(4H,m); 2.88–3.08 (2H,q); 3.24–3.60(1H,s); 3.97–4.21(2H,q); 7.13–7.29 (2H,m); 7.41(1H,d); 7.63 (1H,s); 7.80(1H,d); 15.02 (1H,s). |
| 12 | Yellow oil | 0.99(3H,t); 1.32(3H,t); 1.44–1.72(2H,m); 2.72–3.04 (6H,m); 3.24–3.52(1H,m); 4.00–4.23(2H,q); 7.17–7.44 (3H,m); 7.72(2H,m); 15.14 (1H,s). |
| 13 | Colourless oil | 1.01(3H,t); 1.32(3H,t); 1.48–1.76(2H,m); 2.80–3.07 (6H,m); 3.68–3.99(1H,m); 3.99–4.23(2H,q); 7.08–7.44 (4H,m); 7.78(1H,d); 15.23 (1H,s). |
| 14 | Colourless oil | 0.99(3H,t); 1.32(3H,t); ca 1.60(2H,m); 2.75–3.61(7H, m); 4.11(2H,q); 6.73(1H,m); 7.12–7.53(3H,m); 7.61(1H, d); 15.10(1H,s). |
| 15 | Yellow oil | 1.09(3H,t); 1.34(3H,t); 1.68(2H,m); 2.38(3H,s); 2.5–3.8(7H,m); 3.71(3H,s); 4.13(2H,q); 7.05–7.58(4H, m); 15.31(1H,s). |
| 16 | Yellow oil | 1.01(3H,t); 1.32(3H,t); |

TABLE 6-continued

| Compound No | Appearance | Proton Chemical Shift (CDCl$_3$; δ in ppm) |
|---|---|---|
| | | 1.68(2H,m); 2.37(3H,s); 2.4–3.7(7H,m); 3.64(3H,s); 4.12(2H,q); 6.95–7.58(4H, m); 14.97(1H,brs). |
| 17 | Low melting solid | 1.01(3H,t); 1.30(3H,t); 1.33(6H,s); 1.66(2H,m); 2.0–3.30(7H,m); 2.22(6H,s); 2.38(6H,s); 2.49(3H,s); 4.01(2H,q); 15.0–15.5(1H, brs). |
| 18 | Yellow solid, mp 70° C. | 0.96(3H,t); 1.32(3H,t); 1.58(2H,m); 2.5–4.0(7H,m); 4.11(2H,q); 6.46(1H,s); 7.2–7.6(4H,m); 15.21(1H,s). |
| 19 | White solid, mp 136° C. | 1.02(3H,t); 1.32(3H,t); 1.64 (2H,m); 2.27(3H,s); 2.36(3H, s); 2.42(3H,s); 2.4–4.0(7H,m); 4.12(2H,q); 6.72(1H,d); 7.51 (1H,d); 15.09(1H,s). |
| 20 | Yellow solid, mp 154° C. | 1.02(3H,t); 1.34(3H,t); 1.64 (2H,m); 2.29(3H,s); 2.39 (3H,s); 2.46(3H,s); 2.58(3H, s); 2.4–4.0(7H,m); 4.13(2H,q); 7.51(1H,s); OH not observed. |
| 21 | Yellow oil | 1.02(3H,t); 1.33(3H,t); 1.64 (2H,m); 2.38(3H,s); 2.43(3H, s); 2.4–4.1(7H,m); 4.13(2H,q); 6.77(1H,d); 7.61(1H,d); 15.18 (1H,s). |
| 22 | White solid, mp 110° C. | 1.02(3H,t); 1.33(3H,t); 1.66 (2H,m); 2.31(3H,s); 2.35(3H, s); 2.45(3H,s); 2.4–4.1(7H,m); 4.12(2H,q); 6.83(1H,d); 7.55 (1H,d); 15.18(1H,s). |
| 23 | Pale yellow oil | 1.02(3H,t); 1.33(3H,t); 1.64(2H,m); 2.40(3H,s); 2.43(3H,s); 2.55(3H,s); 2.4–4.1(7H,m); 4.13(2H,q); 6.78(1H,d); 7.53(1H,d); 15.10(1H,s). |
| 24 | Yellow oil | 1.03(3H,t); 1.61(2H,m); 2.38(3H,s); 2.5–3.8(7H,m); 3.73(3H,s); 4.56(2H,d); 5.31–6.20(3H,m); 7.03–7.60 (4H,m); 14.95(1H,brs). |
| 25 | Yellow oil | 0.98(3H,t); 1.58(2H,m); 2.38(3H,s); 2.3–3.8(8H,m); 3.70(3H,s); 4.65(2H,d); 7.06–7.58(4H,m); OH not observed. |
| 26 | Yellow oil | 0.98(3H,t); 1.58(2H,m); 2.38(3H,m); 2.3–3.8(7H,m); 3.70(3H,s); 4.02–4.96(4H, m); 7.00–7.58 (4H,m); 14.29 (1H,brs). |
| 28 | Pale yellow oil | 0.92(3H,t); 1.11(3H,t); 1.49(2H,m); 2.41(3H,s); 2.4–4.1(7H,m); 3.72(3H,s); 4.02(2H,q); 7.0–8.14(9H,m). |
| 29 | Pale yellow solid | 1.13–1.58(6H,m); 2.88–3.33 (6H,m); 3.79–4.07(1H,m); 4.18(2H,q); 7.34–8.08(4H, m); 15.17(1H,s). |

EXAMPLE 6

This non-limiting example illustrates the preparation of formulations of the compounds of the invention.

(a) Emulsifiable Concentrate

Compound No 19 was dissolved in toluene containing 7% V/V "Teric" N13 and 3% v/v "Kemmat" SC15B to give an emulsifiable concentrate which may be diluted with water to the required concentration to give an aqueous emulsion which may be applied by spraying. ("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No 19 (5 parts by weight) and "Dyapol" PT (1 part by weight) were added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade Mark and "Dyapol" PT is an anionic suspending agent; "Teric" N8 is a product of ethoxylation of nonylphenol).

(c) Emulsifiable Concentrate

Compound No 19 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction.)

(d) Dispersible Powder

Compound No 19 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

(e) High Stength Concentrate

Compound No 19 (99 parts by weight), silica aerogel (0.5 parts by weight) and synthetic amorphous silica (0.5 parts by weight) were blended and ground in a hammer-mill to produce a powder having a particle size less than 200 microns.

(f) Dusting Powder

Compound No 19 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing surface active agent and/or oil, to give aqueous compositions of the required concentration which were used, as described in Examples 7 and 8, in the evaluation of the pre-emergence and post-emergence herbicidal activity of the compounds.

EXAMPLE 7

The pre-emergent herbicidal activity of the compounds of the invention formulated as described in Example 6 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glass house and the effect of the treatment was visually assessed. The results are presented in Table 7 where the damage to plants is rated on a scale of from 0 to 5 where 0 represents from 0 to 10% damage, 1 represents from 11 to 30% damage, 2 represents from 31 to 60%, damage, 3 represents from 61 to 80% damage, 4 represents from 81 to 99% damage and 5 represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 7

PRE-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 11 | 2.0 | 0 | 0 | 3 | 4 | 0 | 0 | 0 | 0 |
| 12 | 1.0 | 0 | 0 | 5 | 0 | 0 | 0 | 0 | 0 |
| 16 | 1.0 | 0 | 0 | 3 | 0 | 0 | 0 | 0 | 0 |
| 19 | 1.0 | 1 | 4 | 4 | 4 | 0 | 0 | 0 | 0 |
| 19 | 0.25 | 1 | 1 | 4 | 3 | 0 | 0 | 0 | 0 |

EXAMPLE 8

The post-emergent herbicidal activity of the compounds of the invention formulated as described in Example 6 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 8 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 8

POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 11 | 2.0 | 0 | 4 | 5 | 5 | 0 | 0 | 0 | 0 |
| 12 | 1.0 | 0 | 5 | 5 | 4 | 0 | 0 | 0 | 0 |
| 13 | 1.0 | 0 | 4 | 3 | 4 | 0 | 0 | 0 | 0 |
| 14 | 1.0 | 0 | 3 | 5 | 5 | 0 | 0 | 0 | 0 |
| 14 | 0.25 | 0 | 2 | 4 | 5 | 0 | 0 | 0 | 0 |
| 16 | 1.0 | 0 | 2 | 4 | 5 | 0 | 0 | 0 | 0 |
| 19 | 1.0 | 4 | 5 | 5 | 5 | 0 | 0 | 0 | 0 |
| 19 | 0.25 | 0 | 5 | 4 | 5 | 0 | 0 | 0 | 0 |
| 19 | 0.063 | 0 | 4 | — | 5 | 0 | 0 | 0 | 0 |
| 29 | 1.0 | 0 | 1 | 4 | 5 | 0 | 0 | 0 | 0 |

EXAMPLE 9

The compounds were formulated for test by mixing an appropriate amount with 5 ml of an emulsion prepared by diluting 160 ml of a solution containing 21.9 g per litre of "Span" 80 and 78.2 g per litre of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 9 below. Damage to test plants was assessed after 14 days on a scale of 0 to 5 wherein 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 9 below. A dash (-) means no experiment was carried out.

The names of the test plants were as follows:

| | |
|---|---|
| Mz | Maize |
| Ww | Winter wheat |
| Rc | Rice |
| Br | Barley |
| Av | Avena fatua |
| Dg | Digitaria sanguinalis |
| Al | Alopecurus myosuroides |
| St | Setaria viridis |
| Ec | Echinochloa crus-galli |
| Sh | Sorghum halepense |
| Ag | Agropyron repens |

TABLE 9

| Compound No | APPLICATION Method | Rate (kg/ha) | TEST PLANT | | | | | | | | | | |
|---|---|---|---|---|---|---|---|---|---|---|---|---|---|
| | | | Mz | Ww | Rc | Br | Av | Dg | Al | St | Ec | Sh | Ag |
| 11 | PRE | 2.0 | 2 | 2 | 5 | — | 3 | 5 | 5 | 4 | 5 | 4 | — |
| 11 | PRE | 0.4 | 0 | 0 | 3 | — | 0 | 4 | 5 | 1 | 3 | 3 | 1 |
| 11 | POST | 2.0 | 2 | 2 | 4 | — | 3 | 2 | 3 | 3 | 4 | 5 | 3 |
| 11 | POST | 0.4 | 1 | 1 | 4 | — | 1 | 1 | 1 | 2 | 4 | 4 | 2 |
| 12 | POST | 0.4 | 4 | 1 | 3 | — | 4 | 4 | 4 | 3 | 4 | 4 | 0 |
| 12 | POST | 0.1 | 2 | 0 | 1 | — | 3 | 5 | 3 | 2 | 3 | 3 | 0 |
| 13 | POST | 2.0 | 4 | 0 | 3 | — | 4 | 4 | 4 | 5 | 5 | 4 | 2 |
| 13 | POST | 0.4 | 4 | 0 | 2 | — | 4 | 1 | 4 | 4 | 4 | 3 | 0 |
| 13 | POST | 0.1 | 0 | 0 | 2 | — | 0 | 0 | 4 | 4 | 4 | 1 | 0 |
| 15 | PRE | 2.0 | 3 | 1 | 4 | — | 3 | 5 | 5 | 5 | 5 | 4 | 4 |
| 15 | PRE | 1.0 | 0 | 1 | 2 | — | 2 | 4 | 5 | 5 | 5 | 3 | 2 |
| 15 | POST | 2.0 | 3 | 2 | 4 | — | 4 | 4 | 2 | 4 | 4 | 4 | 3 |
| 15 | POST | 1.0 | 4 | 0 | 1 | — | 3 | 4 | 1 | 4 | 3 | 4 | 3 |
| 16 | POST | 0.2 | 4 | 2 | 2 | — | 4 | 4 | 4 | 4 | 4 | 4 | 1 |
| 16 | POST | 0.05 | 3 | 0 | 0 | — | 2 | 4 | 3 | 3 | 4 | 0 | 0 |
| 19 | POST | 0.2 | 5 | 0 | 3 | 5 | 5 | 5 | 4 | 5 | 5 | 5 | 1 |
| 19 | POST | 0.1 | 5 | 0 | 3 | 4 | 5 | 5 | 4 | 4 | 4 | 4 | 0 |
| 19 | POST | 0.05 | 4 | 0 | 0 | 1 | 5 | 4 | 4 | 4 | 4 | 4 | 0 |
| 29 | POST | 0.4 | 4 | 0 | 4 | 2 | 4 | 3 | 5 | 4 | 4 | 3 | 0 |
| 29 | POST | 0.2 | 3 | 0 | 4 | 1 | 4 | 1 | 4 | 3 | 4 | 2 | 0 |
| 29 | POST | 0.1 | 1 | 0 | 3 | 0 | 2 | 1 | 3 | 4 | 4 | 3 | 0 |

We claim:
1. A compound according to

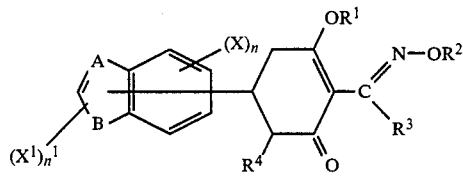

wherein:
A is CH;
B is selected from oxygen and sulfur;
X, which may be the same or different, and $X^1$, which may be the same or different, are independently selected from the group consisting of halogen, $C_1$ to $C_6$ alkyl, $C_1$ to $C_6$ alkanoyl, sulfamoyl; N-($C_1$ to $C_6$ alkyl)sulfamoyl; N,N-di($C_1$ to $C_6$ alkyl)sulfamoyl and the group of the formula —C($R^7$)=$NR^8$ wherein $R^7$ is selected from hydrogen and $C_1$ to $C_5$ alkyl and $R^8$ is selected from hydroxy and $C_1$ to $C_6$ alkoxy;
$R^1$ is selected from the group consisting of: hydrogen; $C_2$ to $C_6$ alkanoyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy; benzenesulfonyl and substituted benzenesulfonyl wherein the benzene ring is substituted with from one to three substituents selected from the group consisting of halogen, nitro, $C_1$ to $C_6$ alkyl and $C_1$ to $C_6$ alkoxy; and an inorganic or an organic cation selected from potassium, lithium, sodium, magnesium, calcium, barium, manganese, copper, zinc, iron, nickel, cobalt and silver, the ammonium ion and the tri- and tetra-(alkyl)ammonium ions wherein alkyl is selected from $C_1$ to $C_6$ alkyl and $C_1$ to $C_6$ hydroxyalkyl;
$R^2$ is selected from the group consisting of: $C_1$ to $C_6$ alkyl, $C_2$ to $C_6$ alkenyl, $C_2$ to $C_6$ alkynyl, $C_1$ to $C_6$ haloalkyl, $C_2$ to $C_6$ haloalkenyl and $C_2$ to $C_6$ haloalkynyl;
$R^3$ is selected from $C_1$ to $C_6$ alkyl;
$R^4$ is hydrogen;
n is zero or an integer selected from 1 to 4; and
$n^1$ is zero or an integer selected from 1 to 3.

2. A compound according to claim 1 wherein A is —CH— and B is oxygen.

3. A compound according to claim 1 of formula

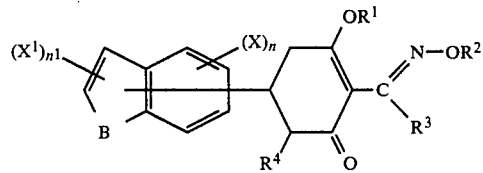

wherein:
B is selected from oxygen and sulfur and N-Z wherein Z is selected from hydrogen and $C_1$ to $C_6$ alkyl;
X, which may be the same or different, and $X^1$, which may be the same or different, are independently selected from the group consisting of halogen, $C_1$ to $C_6$ alkyl, $C_1$ to $C_6$ alkoxy, $C_1$ to $C_6$ alkylthio and $C_2$ to $C_6$ alkanoyl;
$R^1$ is selected from the group consisting of hydrogen, benzoyl and the alkali metals lithium, potassium and sodium;
$R^2$ is selected from the group consisting of $C_1$ to $C_6$ alkyl, $C_1$ to $C_6$ haloalkyl, $C_2$ to $C_6$ alkenyl and $C_2$ to $C_6$ alkynyl;
$R^3$ is selected from the group consisting of $C_1$ to $C_6$ alkyl;
$R^4$ is hydrogen;
n is zero or an integer selected from 1 to 4; and
$n^1$ is zero or an integer from 1 and 2.

4. A compound according to claim 3 of formula

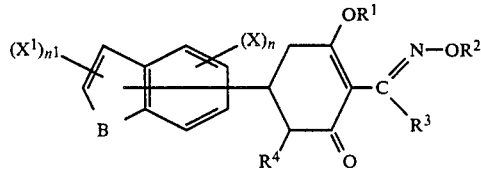

wherein:

B is selected from oxygen and sulfur;

X, which may be the same or different, and $X^1$, which may be the same or different, are independently selected from the group consisting of halogen and $C_1$ to $C_3$ alkyl;

$R^1$ is selected from the group consisting of hydrogen and the alkali metals lithium, potassium and sodium;

$R^2$ is selected from the group consisting of $C_1$ to $C_3$ alkyl, $C_1$ to $C_3$ fluoroalkyl, allyl and propargyl;

$R^3$ is selected from the group consisting of $C_1$ to $C_3$ alkyl;

$R^4$ is hydrogen;

n is zero or an integer selected from 1 to 3; and n is zero.

5. A compound according to claim 2 wherein:

X and/or $X^1$ are independently selected from chlorine and methyl;

$R^1$ is selected from hydrogen and the alkali metals lithium, potassium and sodium;

$R^2$ is selected from ethyl, fluoroethyl, allyl and propargyl;

$R^3$ is selected from ethyl and n-propyl; and $R^4$ is hydrogen.

6. A compound according to claim 2 which is 2-[1-(ethoxy)iminobutyl]-3-hydroxy-5-(4,5,6-trimethylbenzo[b]furan-7-yl)cyclohex-2-en-1-one.

7. A herbicidal composition comprising as active ingredient a compound as defined according to claim 2 and a carrier therefor.

8. A process for severely damaging or killing unwanted plants which process comprises applying to said plants, or to the growth medium of said plants, an effective amount of a compound as defined according to claim 2.

9. A process for selectively controlling the growth of monocotyledonous weeds in dicotyledonous crops which process comprises applying to said crop, or to the growth medium of said crop, a compound as defined according to claim 2 in an amount sufficient to severely damage or kill said weeks but insufficient to substantially damage said crop.

10. A process according to claim 8 or claim 9 wherein the compound is applied at a rate in the range of from 0.005 to 20 kilograms per hectare.

* * * * *